(12) United States Patent
Chen et al.

(10) Patent No.: US 6,987,302 B1
(45) Date of Patent: Jan. 17, 2006

(54) NANOTUBE WITH AT LEAST A MAGNETIC NANOPARTICLE ATTACHED TO THE NANOTUBE'S EXTERIOR SIDEWALL AND ELECTRONIC DEVICES MADE THEREOF

(76) Inventors: Yingjian Chen, 1123 Wisteria Dr., Fremont, CA (US) 94539; Xiaozhong Dang, 789 Gallegos Ter., Fremont, CA (US) 94539

(*) Notice: Subject to any disclaimer, the term of this patent is extended or adjusted under 35 U.S.C. 154(b) by 4 days.

(21) Appl. No.: 10/611,448

(22) Filed: Jul. 1, 2003

(51) Int. Cl.
H01L 29/76 (2006.01)
H01L 29/94 (2006.01)
H01L 31/062 (2006.01)
H01L 31/113 (2006.01)
H01L 31/119 (2006.01)

(52) U.S. Cl. .................................... 257/368
(58) Field of Classification Search ................ 257/368
See application file for complete search history.

(56) References Cited

U.S. PATENT DOCUMENTS

| | | | |
|---|---|---|---|
| 6,515,339 B2 * | 2/2003 | Shin et al. | 257/368 |
| 6,764,874 B1 * | 7/2004 | Zhang et al. | 438/99 |
| 6,798,127 B2 * | 9/2004 | Mao et al. | 313/311 |
| 6,809,361 B2 * | 10/2004 | Honlein et al. | 257/295 |
| 2001/0019238 A1 | 9/2001 | Dai et al. | |

OTHER PUBLICATIONS

J.Li, et al, Appl. Phys. Lett., vol. 75, p. 367, 1999.
W. Choi et al., Appl. Phys. Lett., vol. 79, p. 3696, 2001.
A. M. Cassell et al., J. Phys. Chem. B. vol. 103, p. 6484, 1999.
I. A. Banerjee, et al., Nano Letters. vol. 3, p. 283, 2003.
K. Jiang, et al., Nano Letters, vol. 3, p. 275, 2003.

* cited by examiner

*Primary Examiner*—Howard Weiss (57) ABSTRACT

Present invention provides enabling methods of integrating novel nanotube elements into semiconductor devices, such as transistor containing electronic device. This is done in a series of process steps, which consist of attaching magnetic nanoparticles to nanotubes, tailoring magnetic nanotubes of selected size (diameter and length), filtration of nanotube to pre-determined sizes, preparing nanotube precursor in aqueous chemicals to form colloidal solutions of proper concentration, dispersing nanotube-containing solutions onto wafer surface, and finally positioning nanotubes at desired locations by magnetically assisted assembly to complete nanotube device structure. The key to this invention is to provide miniature nanotubes with tangible physical properties, in this case, magnetic properties, so that they can be aligned, filtered, and precisely directed to desired locations for device application. Such processes enable nanotubes to be compatible with typical semiconductor wafer processing technologies.

9 Claims, 6 Drawing Sheets

NANOTUBE WITH AT LEAST A MAGNETIC NANOPARTICLE ATTACHED TO THE NANOTUBE'S EXTERIOR SIDEWALL AND ELECTRONIC DEVICES MADE THEREOF

BACKGROUND OF THE INVENTION

1. Field of the Invention

The present invention relates generally to the field of semiconductor devices. More particularly, to the application of carbon nanotube in field effect transistors (FET), and the manufacturing method of producing mass quantity of such transistors at wafer level, while achieving precision positioning of carbon nanotubes as gate channels and interconnects. This invention may also be used to fabricate magnetic random access memory devices.

2. Relevant Background

Carbon nanotube exhibits intriguing electronic properties that give rise to the possibility of being utilized in FETs. As a result of different quantum states depending on the size and chiral structure, nanotubes can behave as semiconductor whose conductivity may be changed by a factor of one million or more, comparable to the change in silicon FET. Because of its tiny size, nanotube used as the gate of FET gives rise to significantly lower power consumption, faster switching speed, and better reliability. Metallic nanotubes have the ability to carry a large current density of $10^9$ A/cm$^2$, which is 1000 times higher than the copper wire. This, along with the superior heat conductivity and temperature stability, make the nanotube one of the most attractive interconnect material at extremely miniature feature size.

In prior art, the functionality of a FET device with nanotube gate was demonstrated with a nanotube randomly disposed between the source and drain electrodes. This is typically achieved by fabrication of source and drain electrodes using conventional semiconductor manufacturing process (photolithography and patterning), followed by random deposition of nanotubes on the same substrate, and relied on chance that a nanotube with the proper alignment would be found. Another alternative method that has been used in prior art is to deposit nanotubes on a substrate first. This is followed by pattern imaging and recognition using scanning electron microscopy, which was then used to guide the fabrication of contact leads around individual nanotube via e-beam lithography. Both of these techniques are not viable approaches of producing large quantity of nanotube-based devices. Both methods are disadvantageous because of the lack of control over the precise positioning and alignment of nanotubes with respect to the rest of device structure, and the lack of ability to select nanotubes of proper diameter, length, and electrical properties (metallic or semiconductive).

In prior art, the methods of growing regular array of vertically oriented nanotubes have been shown. One of these methods involves controlled growth of carbon nanotubes on pre-patterned dots of catalysis. Deposition of nanotubes into channels of anodized aluminum has also been used. Both methods are limited to fabrication of vertically aligned nanotubes. They cannot be used to grow in-plane aligned nanotubes, which are required for transistor applications. There are also significant integration challenges between such preparation techniques and conventional semiconductor processing technology.

Therefore, there is a need in the art for a method of fabrication, selection, and assembly of carbon nanotubes into semiconductor electronic devices, such as a FET device.

SUMMARY OF THE INVENTION

The present invention addresses the above problems by attaching superparamagnetic nanoparticles to the surface activated carbon nanotubes, aligning the nanotubes with magnetic field, which allows tailoring and filtering nanotubes to the selected size and electrical properties, and magnetically assisted assembly of nanotubes by positioning them at desired locations to complete nanotube device structure, as both gates and interconnects.

It is difficult to sort or position conventional nanotubes for the purpose of device fabrication, due to their miniature size and physical properties, which result in the lack of means of maneuvering them. It is easier, however, to process articles with magnetic properties. For example, it is known that magnetic particles response to a magnetic field. They attract or repulse each other depending upon they carry the opposite or the same magnetic charges. Magnetic particles may be separated according to the difference in magnetic moment in response to a field gradient.

There are a number of ways to grow conventional carbon nanotubes. Carbon arc, pulse-laser evaporation using graphite target, or chemical vapor deposition (CVD) using gaseous $CO/H_2$, or acetylene $(C_2H_2)$/ammonia $(NH_3)$, or methane $(CH_4)$ are among typically used reactants. The as-grown nanotubes are typically yarn-like substance with random length and electrical properties. The product usually is a mixture of single wall (SWNT) or multi-wall nanotubes (MWNT). It is also a mixture of metallic or semiconductive nanotubes, depending on the diameter and chirality of the nanotubes. When the CVD deposition technique is combined with substrate of anodized Al with nano-pore structure, nanotubes with relatively well-defined length may be formed. Individual nanotube of such kind may be obtained by removing it from the $Al/Al_2O_3$ template by wet-etching. The patterned-template based process technique may be advantageous in producing relatively short nanotubes with sizes already defined within a certain range. The first step of the invention is attachment of magnetic nanoparticles to the conventionally made nanotubes. The nanotube surface is first activated to generate various functional groups on the nanotube: hydroxyl groups, carboxyl groups, carbonyl groups, or sulfate groups, etc. Attachment of magnetic nanoparticles may be achieved by electrostatic interactions via a polyelectrolyte, or by hydrophobic interchain interactions between the functional groups on the nanotube with the molecular chain on the coating of a magnetic nanoparticle. Selective attachment of magnetic nanoparticles only on both ends of a nanotube is also achievable by first attaching Au nanoparticles on the nanotube wall, which act as masks and inhibit magnetic particle attachment on the sidewall.

For long as-grown nanotubes, some further processing steps are required to tailor its length for device use. As a second step of this invention, a nano-grid technique is used to produce either nanotubes of the length 50–150 nm range suitable for FET gate fabrication, or of the length of microns suitable for interconnects. A grid made of lines of conductive metals (Cu, Au, W, Al, Cr, etc). The width of the lines defines the required length of the nanotubes. The nanotubes, which are dispensed onto the grid surface, are first made to align perpendicular to the grid lines by applying a large aligning field in the same direction. Alternatively, the same can be achieved by scanning a row of Si tips over the grid surface, in order to mechanically align the nanotubes. This procedure is followed by the process to trim away the nanotube segments that lie in between the grid lines. This is done by using a current burning technique, or by oxygen plasma etch from the back of the grid surface, which the nanotubes adhere to. Since the semiconducting nanotubes would be burned at lower current as compare to the metallic nanotubes, the size of semiconducting nanotubes may be tailored without affecting the metallic nanotubes. The long metallic nanotubes with their original length can be easily separated, prior to the more refined filtration.

Once the nanotubes of comparable sizes are made, a step of filtering using a magnetic field gradient is used to further narrow down the size distribution. Powders or colloid of magnetic nanotubes are made to either pass through or spin in a gradient magnetic field produced by a pair of magnets. The field and field gradient is adjusted to separate nanotubes with different values of magnetic moment, and therefore different sizes of nanotubes. The magnetic nanotubes may exhibit superparamagnetic characteristics. They posses magnetic moment upon application of a magnetic field, and remain non-magnetic otherwise, which is desirable for keeping them from agglomeration.

Magnetically filtered nanotubes are made to suspend in aqueous chemicals with suitable surface chemistry and molecular weight to form colloid. Such type of colloid needs to have long shelf-life for storage, which might require constant agitation during storage. It is desirable that this type of solution has the optimal viscosity, and adhesion to silicon-based substrates, so that it can be spin coated onto substrate to form a thin layer of uniform coating, much like photoresist.

During the device fabrication, the nanotube-containing solution is spun onto the substrate (wafer) to form a layer of coating. The surface of the wafer contains structures that are made of magnetic materials, such as patterned hard magnetic pillars or bars. In order to attract and settle the magnetic nanotubes to their desirable locations, mechanical or/and magnetic agitation may be utilized.

BRIEF DESCRIPTION OF THE DRAWINGS

In FIG. 5(a), a permanent or electromagnet is provided to provide a large magnetic field to magnetize the magnetic particles attached to the nanotubes. A pair of split coils is connected so as to have oppositely directed fields along the vertical direction. A tube that carries nanotube solution is provided in between the coils and the magnets. The carbon nanotubes are made to pass through the tube, while the filtered nanotubes of selected size come out from one side. In FIG. 5(b), a concentric distillation device with radial magnetic field and field gradient contains the nanotube mixture. It may be spun at high speed to induce separation of different sized nanotubes, which are then removed through various drainage outlets arranged in a series of radial positions.

DETAILED DESCRIPTION OF THE PREFERRED EMBODIMENTS

The purpose of present invention is providing enabling techniques of integrating novel nanotube elements into semiconductor devices, FET device in particular. This is done in a series of process steps, which consist of attaching magnetic nanoparticles to nanotubes, and tailoring the nanotubes to selected size (diameter and length), filtration of nanotube powders, preparing nanotube precursor in aqueous chemicals to form colloidal solutions of proper concentration, dispersing nanotube-containing solutions onto wafer surface, and finally positioning nanotubes at desired locations by magnetic means to complete nanotube device structure. The key to this invention is to provide miniature nanotubes with tangible physical properties, in this case, magnetic properties, so that they can be aligned, filtered, and precisely directed to desired locations for device application. Such processes enable nanotubes to be compatible with typical semiconductor wafer processing technologies.

Figure 1:
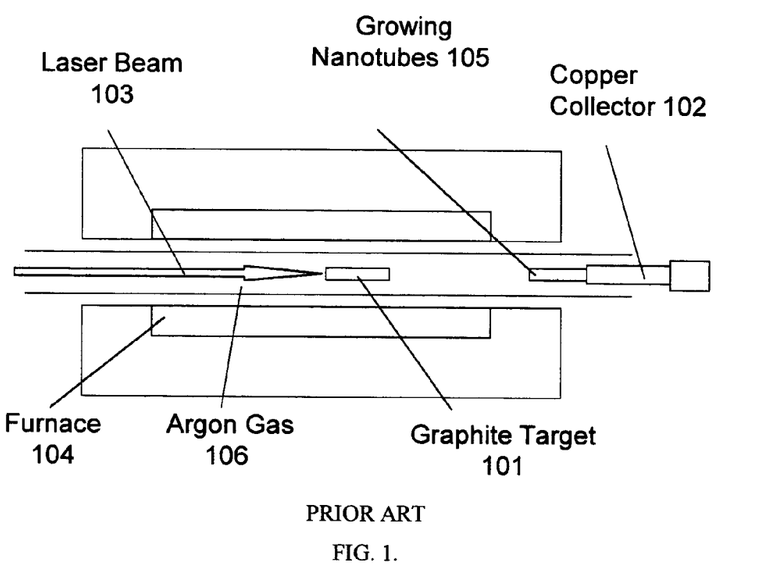
FIG. 1 illustrate one of the prior art methods of produce carbon nanotubes by pulse laser ablation. This method produces high percentage of single wall nanotube (SWNT).

FIG. 1 shows one of the prior art techniques of producing carbon nanotubes by pulse laser ablation. A graphite rod 101 was blasted by intense laser pulses to produce hot carbon gas, which then condenses to form nanotubes, and subsequently deposited on the copper collector 102. The diameters of the nanotubes so produced vary with reaction temperature of the furnace 104. Relatively uniformly sized single-walled nanotubes can be produced by this technique. Another possible fabrication method, which is not shown, produces nanotubes by generating carbon plasma between two graphite rods.

Figure 2:
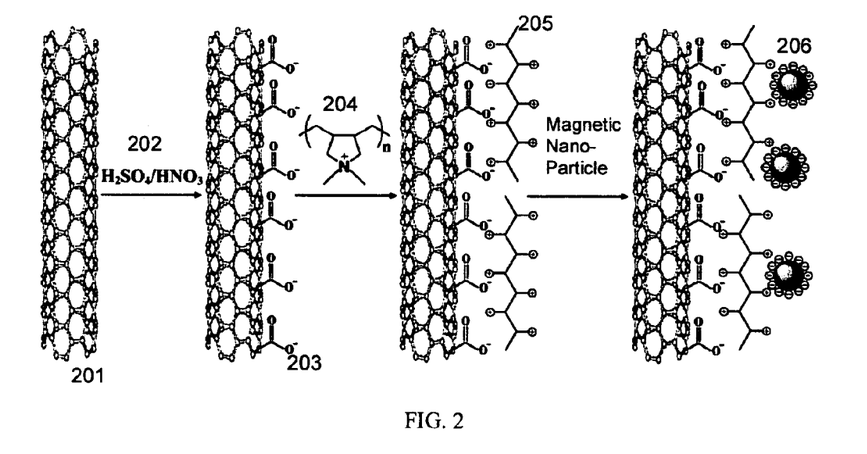
FIG. 2 shows one of the approaches of attaching magnetic nanoparticles to carbon nanotubes. The carbon nanotubes are treated with an $H_2SO_4$—$HNO_3$ solution to activate the surface. Subsequent treatment with a cationic polyelectrolyte results in adsorption of charged polyelectrolyte due to the electrostatic interactions to the carboxyl groups. The nanotubes are subsequently exposed to negatively charged colloidal magnetic nanoparticles, which are anchored to the surface of the nanotubes through the electrostatic interaction.

FIG. 2 shows one of the approaches of attaching magnetic nanoparticles to carbon nanotubes. The carbon nanotubes 201 are treated with an $H_2SO_4$—$HNO_3$ solution 202 to activate the surface. The acid-treatment is used to generate carboxyl 203, carbonyl, hydroxyl, and sulfate groups on the carbon nanotubes. Subsequent treatment with a cationic polyelectrolyte 204 results in adsorption of charged polyelectrolyte 205 due to the electrostatic interactions to the carboxyl groups. The nanotubes are subsequently exposed to negatively charged colloidal magnetic nanoparticles 206, which are anchored to the surface of the nanotubes through the electrostatic interaction. Another alternative approach uses acetone-activated nanotubes. The hydrophobic interactions between the methyl termini of the acetone $CH_3$ and the alkyl chains of octanethiols capped magnetic nanoparticles provide the hydrophobic anchorage. In the case that magnetic nanoparticles are desired only on both ends of the nanotubes, a method is used as mentioned above to attach Au nanocrystals first as protective masks, followed by the step to immobilize magnetic nanoparticles at both ends, and the sidewalls. The Au nanocrystals are chemically etched and the only the magnetic nanoparticles remain attached at the ends of nanotubes.

Figure 3:
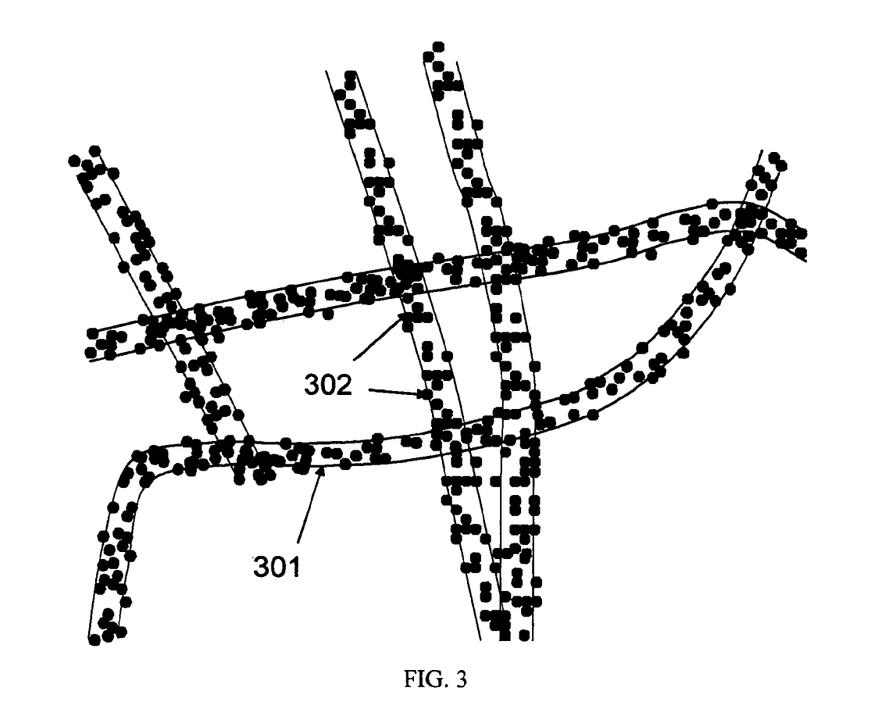
FIG. 3 shows nanotubes with attached magnetic nanoparticles. Because of the tiny size (diameter of 1 nm) of the nanoparticles, they would exhibit superparamagnetism. It does not have measurable moment without applied magnetic field. This helps to keep them separated under normal powder conditions during handling. The nanotubes produced by carbon arc or pulse laser evaporation techniques would be relatively long, as compare to those by chemical vapor deposition.

FIG. 3 shows nanotubes 301 with attached magnetic nanoparticles 302. Because of the tiny size (diameter of <5 nm) of the nanoparticles 302, the magnetic materials 302 would most likely exhibit superparamagnetism. The nanoparticle volume V is estimated to be on the order of 20 $nm^3$. By assuming anisotropy energy $K_u$ of $1\times10^6$ Joul/$m^3$, the value of $K_u$ V/kT is only about 5. If a high $K_u$ of $4\times10^6$ J/$m^3$ is used, this value is about 20. Such low stability factor would result in superparamagnetism of the magnetic nanoparticles. It does not have measurable moment without applied magnetic field. This helps to keep nanotubes separated under normal handling process. The nanotubes produced by carbon arc or pulse laser evaporation techniques would be relatively long, as compare to those by chemical vapor deposition.

Figure 4:
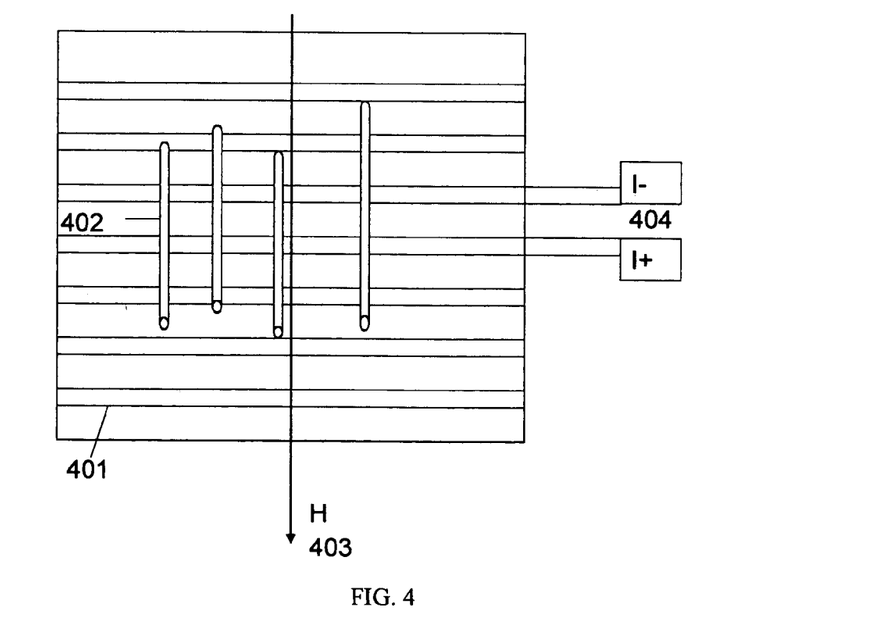
FIG. 4 shows carbon nanotubes dispersed onto a metal grid, which is used to tailor the length of nanotubes to the desirable value for FET device applications. After aligning the long nanotubes by application of a strong magnetic field, or by scanning array of tiny sharp tips along the alignment direction, nanotubes are aligned in perpendicular to the grid lines. The segments that lie in between the grid lines can be burned off upon applying electric current between neighboring grid lines. The nanotubes may be selectively burned off depending upon their conductivity. Alternatively, they can also be etched away in oxygen plasma using the grid line metals as masks.

FIG. 4 illustrates the method and apparatus of tailoring the nanotube size suitable for device use, especially in the case that the as-grown nanotubes are relatively long. A nano-grid technique is used in this case to produce nanotubes of the length 50–150 nm range suitable for FET gate fabrication. A grid, as shown in FIG. 3, is made of lines 401 of conductive metals (Cu, Au, W, Al, Cr, etc). The width of the lines determines the required length of the nanotubes. The nanotubes, 402 which are dispensed onto the grid surface, are first made to align perpendicular to the grid lines by applying a large aligning field 403 in the same direction. Alternatively, the same can be achieved by scanning a row of Si tips over the grid surface, in order to mechanically align the nanotubes. This procedure is followed by the process to trim away the nanotube segments that lie in between the grid lines. This may be done by using a current burning technique. A current or current pulse is applied between the neighboring grid lines 404. Initially the current passes through the nanotube segments that bridge between the grid lines, until a sufficiently large current burn them apart. The integrity of the grid lines 401 is maintained due to their much larger cross-section area, as compare to nanotubes 402. The nanotube segments that lie directly on top of the grid lines are preserved, since they experience no voltage drop. Alternatively a process of oxygen plasma etch may be used to remove the nanotube segments between the grid lines by etching from the opposite of the grid surface that the nanotubes adhere to. Previous studies showed that carbon nanotubes can be metallic or semiconducting, depending on their diameter and chiral angle. Conventional growth techniques generally yield a mixture of the above. The method described in this invention may be used to separate them. Since the semiconducting nanotubes would be burned at lower current as compare to the metallic nanotubes, the size of semiconducting nanotubes may be tailored without affecting the metallic nanotubes. The long metallic nanotubes with their original length can be easily filtered out, prior to the more refined filtration as described below.

Figure 5:
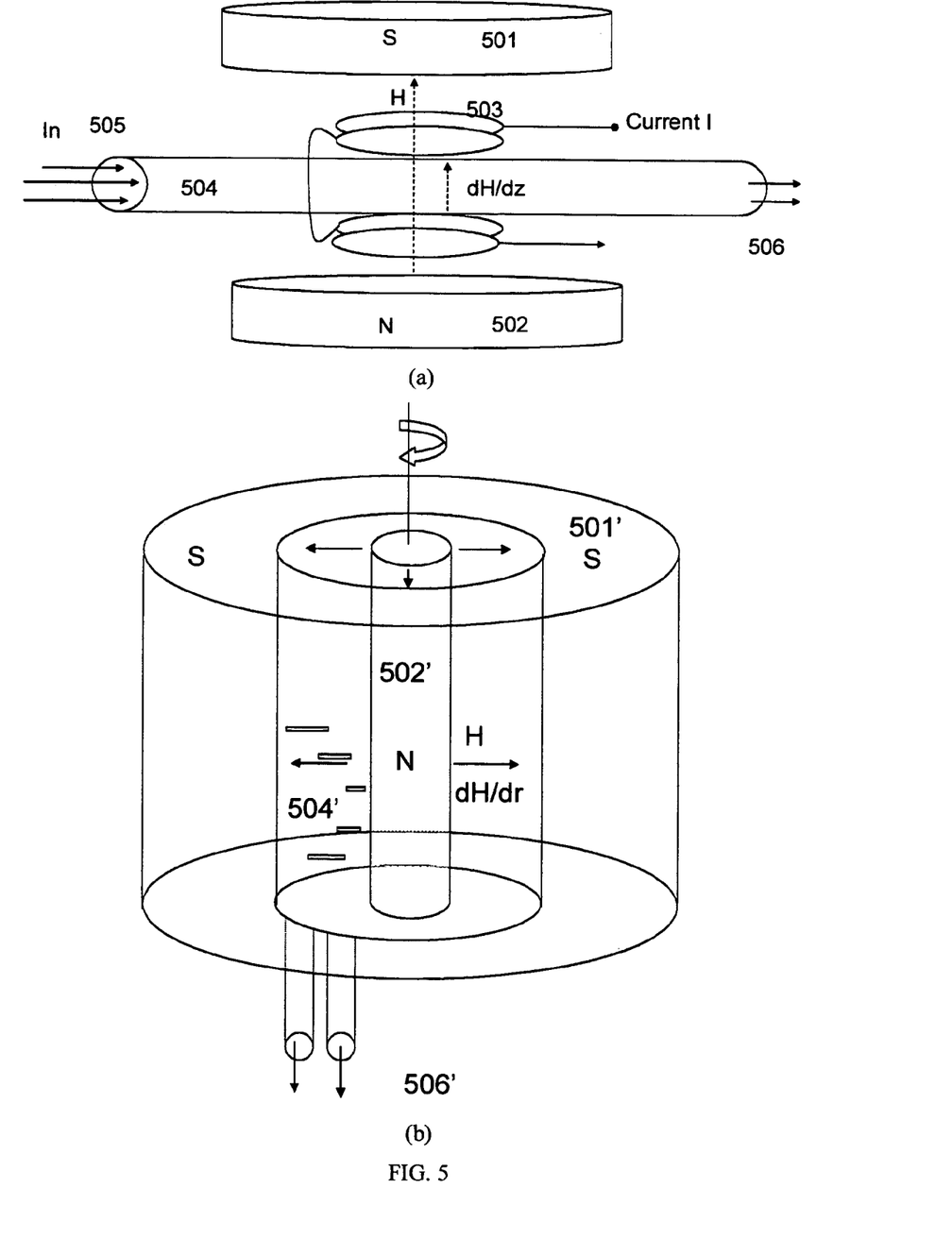
FIG. 5 illustrates examples of apparatus for filtrating and separating nanotubes of different sizes.

FIG. 5 shows two examples of apparatus for the purpose of nanotube filtration. Once the nanotubes of comparable sizes are made, either by growth of nanotubes using patterned template techniques, or by tailoring of long as-grown nanotubes, the filtration step could be used to further reduce the size distribution. The magnetic nanotubes may exhibit superparamagnetic characteristics. They posses magnetic moment only upon application of a magnetic field, and remain non-magnetic otherwise. Superparamagnetism is desirable for keeping magnetic nanotubes from agglomeration. In FIG. 5($a$), powders or solution of magnetic nanotubes are made to pass through a tube device. A set of permanent or electromagnet 501, 502 is provided to induce a large magnetic field to magnetize the magnetic nanotubes. A pair of split coils 503 is connected so as to have oppositely directed fields along the vertical direction. A tube 504 that carries nanotube powder or solution is provided in between the coils and the magnets. The carbon nanotubes 505 are made to pass through the tube, while the filtered nanotubes 506 of selected size come out from one side. The field and field gradient is adjusted to suspend only the nanotubes of predetermined magnetic moment, and thus the predetermined size of nanotubes. Assuming a magnetic moment of m ($\propto$l) is induced by a field H in a superparamagnetic nanotube. It is also assumed that H is sufficient to reach magnetic saturation of the nanotube. The magnetic force that is experience by the nanotube in a magnetic field gradient is given by F=m(dH/dz), which is proportional to the length of the nanotube. If the nanotube containing solution is made to pass the tube at a certain flow rate, only nanotubes of certain size is allowed to pass-through because of their suspension force. Nanotubes of all other sizes are trapped onto the tube walls, which can also be made weakly magnetic. Upon removal of magnetic field, those trapped species may be flushed out with a cleansing solution. Alternatively, nanotubes of different sizes may flow through the distillation pipe, separated into laminar layers, and are removed accordingly. In FIG. 5($b$), another example of such distillation apparatus is shown. A concentric distillation device with radial magnetic field and field gradient contains the nanotube mixture 504'. It may be spun at a speed to induce separation of different sized nanotubes, which are then removed through various drainage outlets 506' arranged in a series of radial positions.

Figure 6:
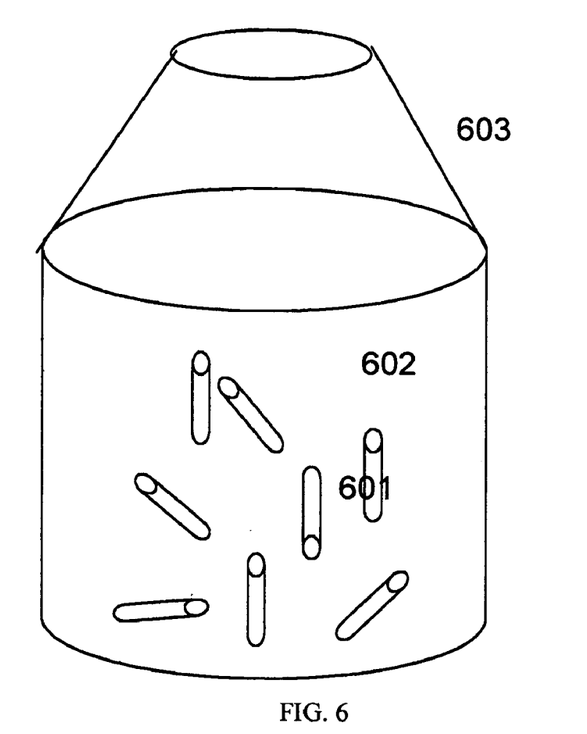
FIG. 6 shows nanotubes with tailored length are dispersed in aqueous chemicals to form colloidal solution. The solution is stored in a container which may be frequently agitated to avoid agglomeration.

FIG. 6 shows that the magnetically filtered nanotubes 601 are made to suspend in aqueous chemicals 602 with suitable molecular weight to form colloidal solution. Such type of colloidal solution needs to have long shelf-life for storage, which might require constant agitation during storage. It is desirable that this type of solution has the optimal viscosity, and adhesion to silicon-based substrates, so that it can be spin coated onto substrate to form a thin layer of uniform coating, much like photoresist. It is also desirable to achieve an optimal concentration of nanotubes in the colloidal solution, in order to provide, in average, certain population of nanotubes in the vicinity of each device. Higher than optimal concentration may result in agglomeration or the tendency of having excess number of nanotubes attached to the permanent magnet position guide, as described in the next paragraph. Less than optimal concentration, on the other hand, would result in difficulty of ensuring full occupancy of nanotubes at allocated sites. The nanotube concentration may be optimized based upon the device density on a wafer, as well as the spin coated solution thickness.

Figure 7:
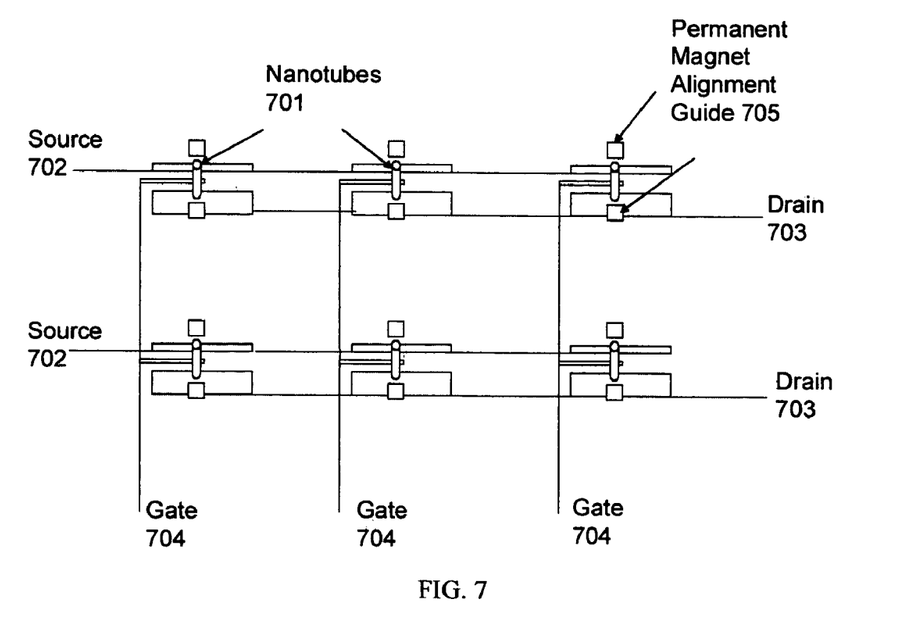
FIG. 7 illustrates 6 FET devices which contain nanotubes as their gate lines. The nanotubes lie between and are electrically contacting source and drain electrodes. A pair of permanent magnetic elements is located at each FET device to guide the position of a magnetic nanotube.

FIG. 7 illustrates a top view of several FET transistors which incorporate carbon nanotube gate during the fabrication stage. The colloidal solution containing carbon nanotubes with magnetic nanoparticles is first spun onto the substrate (wafer) to form a thin layer of coating. The surface of the wafer contains structures 705 that are made of magnetic materials, such as patterned hard magnetic pillars or bars. In order to attract and settle the magnetic nanotubes 701 to their desirable locations, mechanical or/and magnetic agitation may be utilized. During this process, a constant or alternating magnetic field may be applied to magnetize the nanotubes. The magnetic nanotubes in the vicinity of the patterned permanent magnetic alignment guides (PMAG) possess certain mobility to swim to the energetically favorable locations, which are between the PMAGs. This type of mobility in nano-particle-like elements is analogous to the Brownian motion. A comparison may be made between the above-described method and the well-known Bitter decoration of magnetic field lines, since both techniques are used to position particles according to their magnetic surroundings. After the nanotubes are locked into their desired locations, the attached magnetic nanoparticles may be chemically etched or dissolved from the nanotubes. Also shown in FIG. 7, the conducting lines are connected to the source 702, drain 703, and gate 704 of each device. During operation, the conductivity of the semiconductive nanotube changes depending on the applied voltage on the gate electrode 704.

Figure 8:
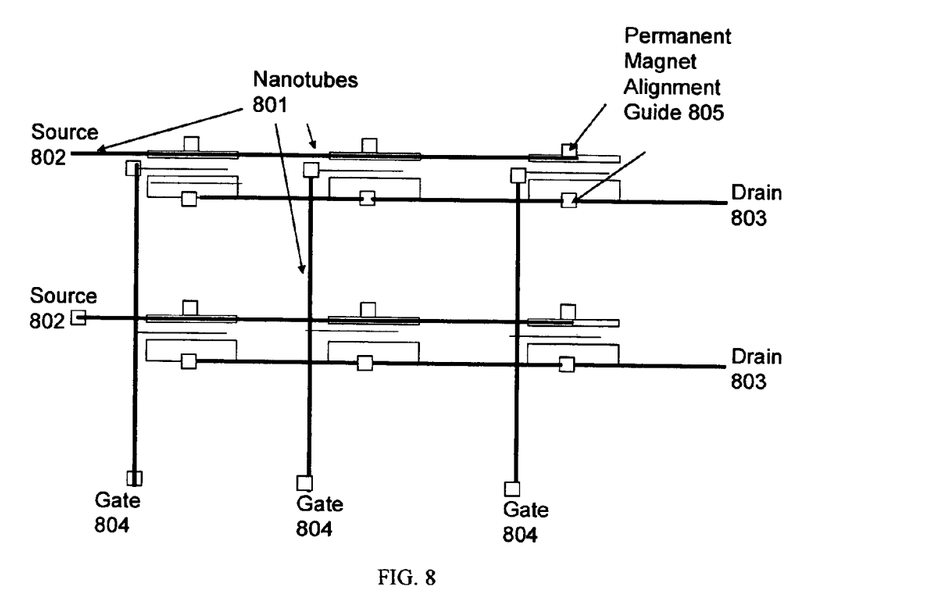
FIG. 8 illustrates 6 FET devices which contain nanotubes as their interconnects. A pair of permanent magnetic elements is located at the ends of a nanotube to guide its position.

FIG. 8 illustrates a top view of several FET transistors which incorporate carbon nanotube interconnects during the fabrication stage. The colloidal solution containing long carbon nanotubes with attached magnetic nanoparticles is first spun onto the substrate (wafer) to form a layer of coating. The surface of the wafer contains structures 805 that are made of magnetic materials, such as patterned hard magnetic pillars or bars. In order to attract and settle the magnetic nanotubes 801 to their desirable locations, mechanical (ultrasonic) or/and magnetic agitation may be utilized. During this process, a constant, alternating, rotating magnetic field, or a combination of those may be applied. The nanotubes with attached magnetic nanoparticles possess certain mobility to be magnetically attracted to the patterned permanent magnetic alignment guides (PMAG) in the vicinity. In order to assemble such relatively long nanotubes for interconnects, it might be desirable to utilize magnetic nanoparticles only at both ends of the nanotubes. In the case that only one nanotube end is attached initially to an element of PMAG, a combination with a rotating or alternating applied magnetic field would be helpful for the nanotubes to find its PMAG target at the other end. This process is carried on for an extended period of time to ensure the complete attachment of interconnects sites. The solution that contains unattached nanotubes is subsequently removed. Finally the attached magnetic nanoparticles may be chemically etched or dissolved from their nanotube host.

Figure 9:
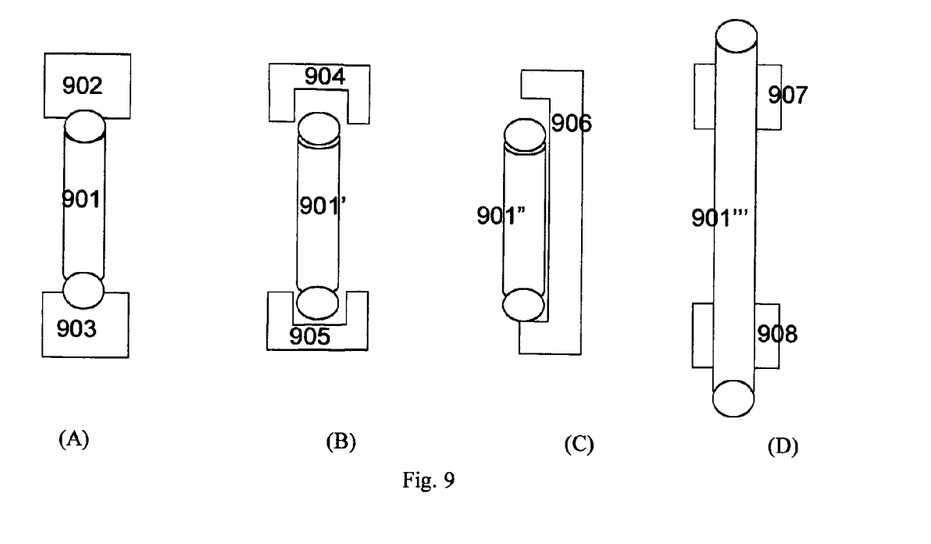
FIG. 9 shows some of the possible configurations of the permanent magnetic elements to effectively position and hold the magnetic nanotube at its desired location. (A) illustrates a pair of simple magnetized permanent magnetic dots. (B) shows a pair of U-shaped permanent magnetic elements. (C) shows a permanent magnetic bar, whose ends hold a nanotube. (D) shows an example that the length of a nanotube exceeds the distance between the two permanent magnetic guide elements.

FIG. 9 shows examples of possible configurations of the permanent magnetic alignment guide for attracting and holding the magnetic nanotube 901, 901', 901", 901''' at its desired location. The examples of nanotubes shown here have magnetic nanoparticles attached to their ends. FIG. 9(A) illustrates a pair of simple magnetized permanent magnetic dots 902, 903. FIG. 9(B) is a pair of U-shaped permanent magnetic elements 904, 905. FIG. 9(C) shows a permanent magnetic bar 906, whose ends hold a nanotube. FIG. 9(D) shows an example of a nanotube which is slightly longer than the length of the pair of PMAG that holds it. These permanent magnetic elements are fabricated in some prior process steps, and are subsequently initialized using a strong magnetic field. The direction of this initialization is in the same direction of intended nanotube direction. The positive and negative magnetic charges between the space of the two elements create a stable low energy location for nanotube to be positioned at. The materials that are used for the elements have large coercive force and high magnetic moment. As a result, they are magnetically stable, and can generate sufficiently strong local magnetic field to attract magnetic nanotubes.

Figure 10:
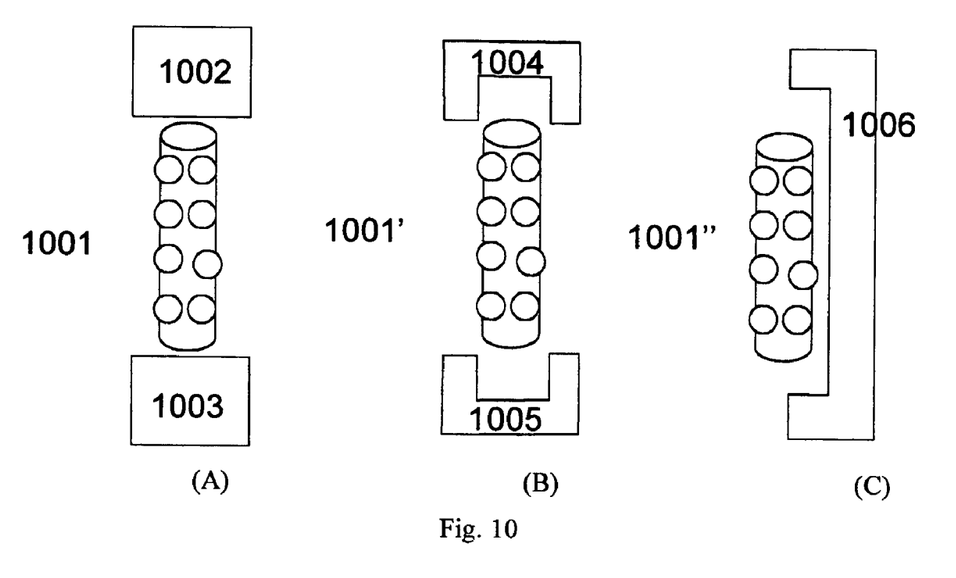
FIG. 10 shows examples of possible configurations of the permanent magnetic alignment guide for attracting and holding the magnetic nanotubes, 1001, 1001', 1001" at their respective desired locations. In contrast to those shown in FIG. 9, the nanotubes in FIG. 10 have magnetic nanotubes attached to their sidewalls. (A) illustrates a pair of simple magnetized permanent magnetic dots. (B) shows a pair of U-shaped permanent magnetic elements. (C) shows a permanent magnetic bar.

FIG. 10 shows examples of possible configurations of the permanent magnetic alignment guide for attracting and holding the magnetic nanotubes 1001, 1001', 1001" at their respective desired locations. In contrast to those shown in FIG. 9, the nanotubes in FIG. 10 have magnetic nanotubes attached to their sidewalls.

Although the invention has been described and illustrated with a certain degree of particularity, it is understood that the present disclosure has been made only by way of example, and that certain changes in the combination and arrangement of parts can be resorted to by those skilled in the art without departing from the spirit and scope of the invention, as hereinafter claimed. For example, the configuration and detailed design of the permanent magnetic alignment guide can be varied significantly to practice the invention as will be readily appreciated by those skilled in the art.

What is claimed is:

1. A device comprising:
    a nanotube having a substantially hollow cylindrical shape, wherein said nanotube has an exterior and interior cylindrical surfaces, said exterior cylindrical surface has a diameter that is less than one micron, said nanotube has two ends, and a length between the two ends measured in a direction perpendicular to the diameter; and
    a magnetic nanoparticle that is attached to the exterior cylindrical surface of the nanotube, the magnetic nanoparticle having a longest dimension that is less than one micron.

2. The device of claim 1, further comprising a plurality of magnetic nanoparticles that are that are attached to the exterior cylindrical surface of the nanotube.

3. The device of claim 2, wherein the magnetic nanoparticles are superparamagnetic.

4. The device of claim 1, wherein the nanoparticle contains an element selected from the group consisting of cobalt, nickel and iron.

5. The device of claim 1, wherein the nanoparticle is attached to the nanotube by an electrostatic or hydrophobic interaction with a carbonyl, carboxyl, hydroxyl or sulfate functional group.

6. A transistor comprising:
a source;
a drain;
a gate;
a channel, the channel including a nanotube having a substantially hollow cylindrical shape, wherein said nanotube has an exterior and interior cylindrical surfaces, said exterior cylindrical surface has a diameter that is less than one micron, said nanotube has two ends, and a length between the two ends measured in a direction perpendicular to the diameter, and the nanotube is disposed between the source and the drain; and is substantially aligned along the shortest distance between the source and the drain, and the nanotube has at least one magnetic nanoparticle attached to the exterior cylindrical surface.

7. A sensor device for detecting biological or chemical molecules comprising:
a plurality of conductive electrodes;
a single or plurality of nanotube channels connecting the electrodes, wherein the nanotubes having substantially hollow cylindrical shape, wherein said nanotube has an exterior and interior cylindrical surfaces, said exterior cylindrical surface has a diameter that is less than one micron, said nanotube has two ends, and a length between the two ends measured in a direction perpendicular to the diameter, said nanotube channels are substantially aligned with each other and with respect to the edges of the electrodes, and each nanotube has at least one magnetic nanoparticle attached to the exterior cylindrical surface.

8. An electronic apparatus comprising
a plurality of electronic devices; and
a plurality of conductive interconnects that are connected between the electronic devices, each of the conductive interconnects including a nanotube having a substantially hollow cylindrical shape, wherein said nanotube has an exterior and interior cylindrical surfaces, said exterior cylindrical surface has a diameter that is less than one micron, said nanotube has two ends, and a length between the two ends measured in a direction perpendicular to the diameter, the length being greater than the diameter, and each nanotube has at least one magnetic nanoparticle attached to the exterior cylindrical surface.

9. The electronic apparatus of claim 8, wherein the electronic devices include a magnetic random access memory (MRAM) cell.

* * * * *